US010792643B2

(12) United States Patent
Tateno et al.

(10) Patent No.: US 10,792,643 B2
(45) Date of Patent: Oct. 6, 2020

(54) METHOD FOR PRODUCING OXIDE CATALYST AND METHOD FOR PRODUCING UNSATURATED NITRILE

(71) Applicant: ASAHI KASEI KABUSHIKI KAISHA, Tokyo (JP)

(72) Inventors: Eri Tateno, Tokyo (JP); Minoru Kadowaki, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/305,782

(22) PCT Filed: Jul. 28, 2017

(86) PCT No.: PCT/JP2017/027510
§ 371 (c)(1),
(2) Date: Nov. 29, 2018

(87) PCT Pub. No.: WO2018/025774
PCT Pub. Date: Feb. 8, 2018

(65) Prior Publication Data
US 2019/0143304 A1 May 16, 2019

(30) Foreign Application Priority Data

Aug. 2, 2016 (JP) .................................. 2016-151880

(51) Int. Cl.
B01J 23/00 (2006.01)
B01J 37/04 (2006.01)
B01J 37/08 (2006.01)
B01J 37/12 (2006.01)
C07C 255/08 (2006.01)
B01J 23/28 (2006.01)
B01J 23/20 (2006.01)
C07C 51/215 (2006.01)
B01J 23/18 (2006.01)
B01J 37/03 (2006.01)
C07C 253/24 (2006.01)
C07C 253/26 (2006.01)
C07B 61/00 (2006.01)

(52) U.S. Cl.
CPC ............. B01J 23/002 (2013.01); B01J 23/18 (2013.01); B01J 23/20 (2013.01); B01J 23/28 (2013.01); B01J 37/03 (2013.01); B01J 37/04 (2013.01); B01J 37/08 (2013.01); B01J 37/12 (2013.01); C07C 51/215 (2013.01); C07C 253/24 (2013.01); C07C 253/26 (2013.01); C07C 255/08 (2013.01); B01J 2523/00 (2013.01); B01J 2523/53 (2013.01); B01J 2523/55 (2013.01); B01J 2523/56 (2013.01); B01J 2523/68 (2013.01); C07B 61/00 (2013.01); Y02P 20/52 (2015.11)

(58) Field of Classification Search
CPC . B01J 23/002; B01J 23/18; B01J 23/20; B01J 23/28; B01J 37/03; B01J 37/04; B01J 37/08; B01J 37/12; C07C 51/215; C07C 253/24; C07C 253/26; C07C 255/08
See application file for complete search history.

(56) References Cited

U.S. PATENT DOCUMENTS

| 6,432,870 B1 | 8/2002 | Tu et al. |
| 2006/0235238 A1 | 10/2006 | Komada et al. |
| 2011/0218352 A1 | 9/2011 | Besecker et al. |
| 2013/0253217 A1 | 9/2013 | Ishii et al. |
| 2015/0231604 A1 | 8/2015 | Ishii et al. |
| 2016/0297753 A1 | 10/2016 | Ishii et al. |

FOREIGN PATENT DOCUMENTS

| EP | 3278874 A1 | 2/2018 |
| JP | 11-285636 A | 10/1999 |
| JP | 2003-71284 A | 3/2003 |
| JP | 3938225 B2 | 6/2007 |
| JP | 2009-183897 A | 8/2009 |
| JP | 2011-529777 A | 12/2011 |
| WO | WO 2004/108278 A1 | 12/2004 |
| WO | WO 2014/050615 A1 | 4/2014 |
| WO | WO 2015/133510 A1 | 9/2015 |

OTHER PUBLICATIONS

International Search Report (PCT/ISA/210) issued in PCT/JP2017/027510, dated Oct. 17, 2017.
European Search Report dated Jul. 9, 2019, for European Application No. 17836879.1.

Primary Examiner — James A Fiorito
(74) Attorney, Agent, or Firm — Birch, Stewart, Kolasch & Birch, LLP

(57) ABSTRACT

A method for producing an oxide catalyst containing Mo, V, Sb, and Nb, the method including:
  a raw material preparation step including
    sub-step (I) of preparing an aqueous mixed liquid (A) containing Mo, V, and Sb,
    sub-step (II) of adding hydrogen peroxide to the aqueous mixed liquid (A), thereby facilitating oxidation of the aqueous mixed liquid (A) and obtaining an aqueous mixed liquid (A'), and
    sub-step (III) of mixing the aqueous mixed liquid (A') and a Nb raw material liquid (B), thereby obtaining an aqueous mixed liquid (C);
  a drying step of drying the aqueous mixed liquid (C), thereby obtaining a dried powder; and
  a calcination step of calcining the dried powder under an inert gas atmosphere,
  wherein a time elapsed from addition of the hydrogen peroxide to the aqueous mixed liquid (A) to mixing the Nb raw material liquid (B) therewith is less than 5 minutes and
  the aqueous mixed liquid (A') before being subjected to the sub-step (III) has an oxidation-reduction potential of 150 to 350 mV.

5 Claims, No Drawings

METHOD FOR PRODUCING OXIDE CATALYST AND METHOD FOR PRODUCING UNSATURATED NITRILE

TECHNICAL FIELD

The present invention relates to a method for producing an oxide catalyst and a method for producing an unsaturated nitrile.

BACKGROUND ART

Currently, unsaturated nitriles generally sold on the market are for the most part industrially produced through a catalytic ammoxidation reaction of an olefin, ammonia, and oxygen. On the other hand, in recent years, a method for producing an unsaturated nitrile corresponding to a raw material, the method using as the raw material an alkane such as propane or isobutane in place of the olefin and using a gas-phase catalytic ammoxidation reaction, has been drawing attention, and a large number of catalysts for use on that occasion have also been proposed.

For example, Patent Literature 1 describes a method for producing, as a catalyst for a gas-phase catalytic oxidation or gas-phase catalytic ammoxidation of propane or isobutane, a catalyst containing: at least one element selected from tellurium and antimony; molybdenum; vanadium; and niobium, in which a niobium raw material liquid containing niobium and a carboxylic acid is used.

In addition, Patent Literature 2 describes a method for producing a catalyst containing molybdenum, vanadium, and niobium, in which an aqueous mixed liquid containing the above-described elements is subjected to aging for 90 minutes or more and 50 hours or less under an atmosphere having an oxygen concentration of 1 to 25 vol %.

Further, Patent Literature 3 describes an oxide catalyst containing an oxide containing as constituent elements molybdenum (Mo), vanadium (V), niobium (Nb), and antimony (Sb) each in a particular atomic ratio, the oxide catalyst having a reduction rate of 8 to 12% and a specific surface area of 5 to 30 m$^2$/g, and a method for producing the oxide catalyst.

CITATION LIST

Patent Literature

Patent Literature 1: Japanese Patent No. 3938225
Patent Literature 2: Japanese Patent Laid-Open No. 2009-183897
Patent Literature 3: International Publication No. WO 2004/108278

SUMMARY OF INVENTION

Technical Problem

According to the methods for producing a catalyst described in Patent Literatures 1 to 3, an ammoxidation reaction catalyst to endure the use under particular conditions is obtained, but it cannot be deemed that the yield of an unsaturated nitrile in a case where the resultant catalyst is used is industrially sufficient.

Thus, an object of the present invention is to provide a method by which an oxide catalyst giving a high unsaturated nitrile yield can be produced without the need for introducing a complicated step and changing facilities.

Solution to Problem

The present inventors have conducted diligent studies to solve the problems of the conventional techniques to find that when a method for producing a catalyst, which is to be used for a gas-phase catalytic oxidation or gas-phase catalytic ammoxidation of propane or isobutane and which comprises molybdenum, vanadium, antimony, and niobium, comprises: a raw material preparation step; a drying step; and a calcination step, wherein in the preparation step, the oxidation-reduction potential of an aqueous mixed liquid comprising molybdenum and vanadium is adjusted in a predetermined range, an oxide catalyst exhibiting high performance can be thereby produced, thereby completing the present invention.

That is, the present invention is as follows.

[1]
A method for producing an oxide catalyst comprising Mo, V, Sb, and Nb, the method comprising:
 a raw material preparation step comprising
  a sub-step (I) of preparing an aqueous mixed liquid (A) comprising Mo, V, and Sb,
  a sub-step (II) of adding hydrogen peroxide to the aqueous mixed liquid (A), thereby facilitating oxidation of the aqueous mixed liquid (A) and obtaining an aqueous mixed liquid (A'), and
  a sub-step (III) of mixing the aqueous mixed liquid (A') and a Nb raw material liquid (B), thereby obtaining an aqueous mixed liquid (C);
 a drying step of drying the aqueous mixed liquid (C), thereby obtaining a dried powder; and
 a calcination step of calcining the dried powder under an inert gas atmosphere,
 wherein a time elapsed from addition of the hydrogen peroxide to the aqueous mixed liquid (A) to mixing the Nb raw material liquid (B) therewith is less than 5 minutes and
 the aqueous mixed liquid (A') before being subjected to sub-step (III) has an oxidation-reduction potential of 150 to 350 mV.
[2]
The method for producing the oxide catalyst according to [1], wherein in the drying step, the aqueous mixed liquid (C) has an oxidation-reduction potential of less than 450 mV.
[3]
The method for producing the oxide catalyst according to [1] or [2], wherein the oxide catalyst is represented by the following formula (1):

$$Mo_1V_aNb_bSb_cT_dZ_eO_n \quad (1)$$

wherein T represents at least one element selected from Ti, W, Mn, and Bi; Z represents at least one element selected from La, Ce, Yb, and Y; a, b, c, d, and e represent atomic ratios of respective elements when an atomic ratio of Mo is 1, and are in a range of 0.05≤a≤0.3, 0.01≤b≤0.15, 0.05≤c≤0.3, 0≤d≤0.1, and 0≤e≤0.1 respectively; and n represents a value satisfying a balance of atomic valences.
[4]
The method for producing the oxide catalyst according to any one of [1] to [3], wherein in the raw material preparation step, a carrier raw material is added to regulate a content of a carrier to be 30% by mass or more and 70% by mass or less based on a total amount of the oxide catalyst.

[5]
A method for producing an unsaturated acid or an unsaturated nitrile, the method comprising:

a step of obtaining the oxide catalyst by the method for producing the oxide catalyst according to any one of [1] to [4]; and a production step wherein a gas-phase catalytic oxidation reaction or a gas-phase catalytic ammoxidation reaction of propane or isobutane are performed in a presence of the produced oxide catalyst to thereby produce an unsaturated acid or an unsaturated nitrile corresponding thereto.

Advantageous Effects of Invention

According to the method for producing an oxide catalyst of the present invention, an oxide catalyst giving a high unsaturated nitrile yield can be produced without the need for introducing a complicated step and changing facilities.

DESCRIPTION OF EMBODIMENTS

Hereinafter, an embodiment for carrying out the present invention (hereinafter, simply referred to as "present embodiment") will be described in detail. The present embodiment, which will be described below, is an example for describing the present invention and is not intended to limit the present invention to the following contents. The present invention can be carried out by being appropriately modified within the range of the scope thereof.

[Method for Producing Oxide Catalyst]

A method for producing an oxide catalyst according to the present embodiment is a method for producing an oxide catalyst comprising Mo, V, Sb, and Nb, and the method comprises: a raw material preparation step comprising sub-step (I) of preparing an aqueous mixed liquid (A) comprising Mo, V, and Sb, sub-step (II) of adding hydrogen peroxide to the aqueous mixed liquid (A), thereby facilitating oxidation of the aqueous mixed liquid (A) and obtaining an aqueous mixed liquid (A'), and sub-step (III) of mixing the aqueous mixed liquid (A') and a Nb raw material liquid (B), thereby obtaining an aqueous mixed liquid (C); a drying step (hereinafter, also referred to as "step (IV)") of drying the aqueous mixed liquid (C), thereby obtaining a dried powder; and a calcination step (hereinafter, also referred to as "step (V)") of calcining the dried powder under an inert gas atmosphere, wherein a time elapsed from addition of the hydrogen peroxide to the aqueous mixed liquid (A) to mixing the Nb raw material liquid (B) therewith is less than 5 minutes, and the aqueous mixed liquid (A') before being subjected to the sub-step (III) has an oxidation-reduction potential of 150 to 350 mV.

The oxide catalyst obtained by the production method according to the present embodiment can be suitably used for a gas-phase catalytic oxidation reaction or gas-phase catalytic ammoxidation reaction of propane or isobutane. Particularly, according to the method for producing an oxide catalyst of the present embodiment, an oxide catalyst giving a high unsaturated nitrile yield can be produced without the need for introducing a complicated step and changing facilities. In addition, "high yield" as referred to herein means that in a case where oxide catalysts each at least having the same or approximately the same composition as the composition represented by formula (1), which will be described later, the yield of resultant acrylonitrile is high.

It is to be noted that the method for producing an oxide catalyst may further comprise a removal step (hereinafter, also referred to as "step (VI)") of removing a protrusion existing at the surface of a particle of the oxide catalyst.

[Sub-Step (I): Step of Preparing Aqueous Mixed Liquid (A)]

Sub-step (I) in the present embodiment is a step of preparing an aqueous mixed liquid (A) comprising Mo, V, and Sb. Examples of the preparation method include, but are not limited to, a method of mixing a Mo-containing raw material (hereinafter, also referred to as "Mo raw material"), a V-containing raw material (hereinafter, also referred to as "V raw material"), and an Sb-containing raw material (hereinafter, also referred to as "Sb raw material"), thereby preparing the aqueous mixed liquid (A). In addition, the method of mixing is not particularly limited, and known mixing methods can be used.

Examples of the Mo raw material include, but are not limited to, ammonium heptamolybdate [$(NH_4)_6Mo_7O_{24} \cdot 4H_2O$], molybdenum trioxide [$MoO_3$], phosphomolybdic acid [$H_3PMo_{12}O_{40}$], silicomolybdic acid [$H_4SiMo_{12}O_{40}$], and molybdenum pentachloride [$MoCl_5$]. Among these, ammonium heptamolybdate [$(NH_4)_6Mo_7O_{24} \cdot 4H_2O$] is preferable.

Examples of the V raw material include, but are not limited to, ammonium metavanadate [$NH_4VO_3$], vanadium pentoxide [$V_2O_5$], and vanadium chlorides [$VCl_4$, $VCl_3$]. Among these, ammonium metavanadate [$NH_4VO_3$] is preferable.

Examples of the Sb raw material include, but are not limited to, antimony oxides [$Sb_2O_3$, $Sb_2O_5$], antimonious acid [$HSbO_2$], antimonic acid [$HSbO_3$], ammonium antimonate [$(NH_4)SbO_3$], antimony chloride [$Sb_2Cl_3$], organic acid salts such as a tartaric acid salt of antimony, and metal antimony. Among these, diantimony trioxide [$Sb_2O_3$] is preferable.

In sub-step (I), the aqueous mixed liquid (A) can be prepared, for example, by adding the above-described Mo raw material, V raw material, and Sb raw material to water and heating a resultant mixture. Further, a Z raw material, which will be described later, may be added. When the aqueous mixed liquid (A) is prepared, the heating temperature and the heating time are preferably adjusted in such a way as to create a state in which respective raw materials are sufficiently soluble. Specifically, the heating temperature is preferably 70° C. or more and 100° C. or less, and the heating time is preferably 30 minutes or more and 5 hours or less. On this occasion, the aqueous mixed liquid (A) is preferably being stirred such that the raw materials easily dissolve. In addition, the atmosphere in preparing the aqueous mixed liquid (A) may be an air atmosphere but can be an inert gas atmosphere from the viewpoint of adjusting the oxidation number of the resultant oxide catalyst. The aqueous mixed liquid (A) is preferably held at a temperature of 20° C. or more and 80° C. or less, more preferably 40° C. or more and 80° C. or less. When the temperature of the aqueous mixed liquid (A) is 20° C. or more, there is a tendency that the precipitation of metal species dissolving in the aqueous mixed liquid (A) is thereby unlikely to occur.

Subsequently, a carrier raw material containing silica sol can be added to the aqueous mixed liquid (A). In the present embodiment, silica sol is preferably added to the aqueous mixed liquid (A) after heating. Silica sol functions as a carrier when it is made into an oxide catalyst. The temperature at the time when silica sol is added is preferably 80° C. or less. In a case where silica sol is added at 80° C. or less, there is a tendency that the stability of the silica sol is relatively high to suppress gelation of the aqueous mixed liquid (C). In a case where silica sol is added to the aqueous mixed liquid (C), the timing may be at the time when aging is started, which will be described later, may be in the middle of aging, or may be immediately before drying the aqueous mixed liquid (C).

[Sub-Step (II): Step of Facilitating Oxidation]

Sub-step (II) in the present embodiment is a step of adding hydrogen peroxide to the aqueous mixed liquid (A), thereby facilitating oxidation of the aqueous mixed liquid (A) and obtaining the aqueous mixed liquid (A'). It is to be noted that examples of the operation that can be carried out together with the addition of hydrogen peroxide and that is for facilitating the oxidation include, but are not limited to, an operation of heating while blowing air. In addition, facilitation of the oxidation can be checked from the fact that when the oxidation-reduction potentials of the aqueous mixed liquid (A) and of the aqueous mixed liquid (A') are compared, the value of the latter is larger than the value of the former. Through this step, the oxidation number of a composite oxide in the resultant oxide catalyst can be adjusted. In sub-step (II) in the present embodiment, the oxidation of the aqueous mixed liquid (A) is preferably facilitated by adding hydrogen peroxide. That is, in the present embodiment, the aqueous mixed liquid (A') is preferably obtained by adding hydrogen peroxide to the aqueous mixed liquid (A). The timing of adding hydrogen peroxide may be before or after heating the aqueous mixed liquid (A). In addition, hydrogen peroxide may be added in the middle of heating. In addition, the addition may be carried out before or after adding silica sol. In addition, hydrogen peroxide may be added to the aqueous mixed liquid (C) or may be separately added to both (A) and (C). From the viewpoint of adjusting the oxidation number of the resultant oxide catalyst in a proper range, the amount of addition of hydrogen peroxide in sub-step (II) is preferably 0.01 or more and 5.0 or less, more preferably 0.1 or more and 3.0 or less, and still more preferably 0.15 or more and 2.5 or less, as a molar ratio of hydrogen peroxide to Sb ($H_2O_2$/Sb).

From the viewpoint of avoiding an excessive increase in the oxidation-reduction potential of the aqueous mixed liquid (A'), the time elapsed from addition of the hydrogen peroxide to the aqueous mixed liquid (A) to mixing the Nb raw material liquid (B) therewith is set to less than 5 minutes, preferably less than 4 minutes and 30 seconds. From the same viewpoint, it is preferable that the heating temperature and the heating time after adding hydrogen peroxide to the aqueous mixed liquid (A) be appropriately adjusted. Specifically, the heating temperature is preferably 20° C. or more and 80° C. or less, and the heating time is preferably less than 5 minutes. The number of rotations during stirring at the time of heating can be adjusted to a moderate number of rotations such that components in a solution disperse easily and uniformly, and it is preferable to keep such stirring state.

[Sub-Step (III): Mixing Step]

Sub-step (III) in the present embodiment is a step of mixing the aqueous mixed liquid (A') and the Nb raw material liquid (B), thereby obtaining an aqueous mixed liquid (C). In a case where the carrier raw material is added, the carrier raw material is preferably added in this step. In the aqueous mixed liquid (A'), the carrier raw material may be mixed in advance. The mixing method is not particularly limited, and known methods can be used. It is to be noted that the carrier raw material refers to a raw material that becomes a carrier in an oxide catalyst, and the Nb raw material liquid (B) refers to a Nb-containing raw material liquid.

The content of the carrier is preferably regulated to be 30% by mass or more and 70% by mass or less based on the total amount of the oxide catalyst. When the content of the carrier is in the above-described range, there is a tendency that the attrition resistance and the catalyst performance of the oxide catalyst are thereby excellent.

The carrier raw material in the present embodiment preferably contains silica sol. Examples of silica sol include acidic sol and basic sol, but any silica sol may be used and basic silica sol is more preferable. The carrier raw material preferably contains 30% by mass or more, more preferably 30% by mass or more and 70% by mass or less, and still more preferably 40% by mass or more and 60% by mass or less, of silica sol in terms of $SiO_2$ based on the total amount (100% by mass) of the carrier raw material.

It is preferable that the carrier raw material further contain powdery silica. This powdery silica becomes part of the silica raw material together with silica sol.

Examples of the carrier raw material include aluminum oxide, titanium oxide, and zirconium oxide in addition to silica sol, powdery silica, and the like. The carrier raw materials may be used singly, or two or more thereof may be used together. A preferred carrier raw material is silica.

In sub-step (III), the silica sol is preferably 30% by mass or more and 70% by mass or less, more preferably 40% by mass or more and 60% by mass or less, and still more preferably 45% by mass or more and 55% by mass or less, in terms of $SiO_2$ based on the total amount (100% by mass) of silica sol and powdery silica. When the silica sol is 30% by mass or more, there is a tendency that deterioration of the attrition resistance of the oxide catalyst is thereby suppressed, and when the silica sol is 70% by mass or less, there is a tendency that deterioration of the performance of the oxide catalyst is thereby suppressed.

Examples of the Nb raw material include, but are not limited to, niobic acid, inorganic acid salts of niobium, and organic acid salts of niobium. Among these, niobic acid is preferable. Niobic acid is represented by formula $Nb_2O_5 \cdot nH_2O$ and is also called a niobium hydroxide or a niobium oxide compound.

The Nb raw material liquid (B) preferably contains water. On this occasion, the ratio between water and Nb contained (Nb (mol)/Water (kg)) is more preferably set to 0.1 or more and 10 or less, still more preferably 0.3 or more and 5.0 or less, from the viewpoint of stabilizing the Nb raw material or other viewpoints. In addition, the Nb raw material may contain an organic acid salt or a free organic acid. The organic acid is not particularly limited, but oxalic acid is preferable. The molar ratio of the organic acid to niobium in the Nb raw material (organic acid/niobium) is preferably 1.0 or more and 4.0 or less.

The method of allowing the Nb raw material liquid (B) to contain water and the organic acid is not particularly limited, and water and the organic acid may be mixed in any order. In addition, the above-described mixing can be performed at an arbitrary temperature as long as the temperature is above the freezing point and below the boiling point of the Nb raw material liquid. Mixing at room temperature is preferable because of easiness of operation. In addition, the Nb raw material containing water may further contain hydrogen peroxide water.

The Nb raw material liquid (B) is preferably prepared by heating and stirring the Nb raw material and a dicarboxylic acid in water. Examples of the dicarboxylic acid include, but are not limited to, oxalic acid [$(COOH)_2$]. Hydrogen peroxide may be added to the Nb raw material liquid (B). On this occasion, the molar ratio of hydrogen peroxide to Nb ($H_2O_2$/Nb) is preferably less than 5.0 from the viewpoint of properly regulating the oxidation-reduction states of the constituent elements of the oxide catalyst, making the catalyst performance of the resultant oxide catalyst proper, and other viewpoints. In addition, the sum of hydrogen peroxide to be added in sub-step (II) and hydrogen peroxide to be added in sub-step (III) is preferably less than 7.0 as a molar ratio of hydrogen peroxide to Sb ($H_2O_2$/Sb).

In addition, the silica raw material may be mixed in the Nb raw material liquid (B) in advance. The order of mixing the Nb raw material liquid (B) and the silica raw material is not particularly limited. The silica raw material may be added to the Nb raw material liquid (B), or the Nb raw material liquid (B) may be added to the silica raw material. Among these, the silica raw material may more preferably be added to the Nb raw material liquid (B) from the viewpoint of suppressing precipitation of Nb in the Nb raw material liquid (B). In addition, a resultant mixture may be left to stand or stirred after the addition, and further, an ultrasonic treatment may be performed with a homogenizer or the like. On this occasion, part of the other metal raw materials may be added to the Nb raw material liquid (B) in advance, or part of the other metal raw materials may be added to the silica raw material in advance. The other metal raw materials refer to the Mo raw material, the V raw material, the Sb raw material, the W raw material, and the Z raw material. In addition, the amount of addition of the other raw materials on this occasion is preferably less than 50% by mass, more preferably 0.0% by mass or more and 40% by mass or less, and still more preferably 0.0% by mass or more and 30% by mass or less, based on the total amount of the metal raw materials which are finally added.

In the present embodiment, the oxidation-reduction potential of the aqueous mixed liquid (A') before being subjected to sub-step (III) is set to 150 to 350 mV. That is, the oxidation-reduction potential of the aqueous mixed liquid (A') in starting the mixing of the aqueous mixed liquid (A') and the Nb raw material liquid (B) is set to 150 to 350 mV. This oxidation-reduction potential indicates oxidation states of mainly Mo, V, and Sb, and when Mo, V, or Sb is in an oxidized state (state in which valence is high), the potential becomes high, and when Mo, V, or Sb is in a reduced state (state in which valence is low), the potential becomes low. The aqueous mixed liquid (A') more preferably has an oxidation-reduction potential of 160 to 330 mV, still more preferably 170 to 320 mV. The oxidation-reduction potential can be measured by inserting an oxidation-reduction potentiometer sold on the market into the aqueous mixed liquid (A) to read a stable numerical value.

In conventional methods for preparing a catalyst, by setting a sufficient heating time after facilitation of the oxidation is started by addition or the like of hydrogen peroxide, the aqueous mixed liquid (A) has been made such that the oxidation of Mo, V, and Sb sufficiently progresses. In a case where No, V, and Sb are sufficiently oxidized, the value of the oxidation-reduction potential of the aqueous mixed liquid (A) becomes larger than 380 mV. However, according to the validation conducted by the present inventors, it has been found that a catalyst giving a higher yield can be obtained when Mo, V, and Sb are in a somewhat reduced state.

The reason that the yield of a desired product is improved when the oxidation-reduction potential of the aqueous mixed liquid (A) is in the above-described range is not clear, but it is inferred that the improvement have a relationship with the degree of reduction of the catalyst. It is considered that in the raw material preparation step in the present embodiment, a liquid phase where the metal components such as Mo, V, and Sb are uniformly dispersed in a state of having a moderate degree of reduction is obtained, and by mixing Nb therein, a catalyst having a uniform and proper degree of reduction can be obtained, resulting in an improvement in the yield.

In the present embodiment, as described above, the carrier raw material can be added in at least one of sub-step (I), sub-step (II), and sub-step (III). That is, in the raw material preparation step, the carrier raw material can be added. Preferably, in the raw material preparation step, the carrier raw material is added to regulate the content of the carrier to be 30% by mass or more and 70% by mass or less based on the total amount of the oxide catalyst.

In at least one of sub-step (I), sub-step (II), and sub-step (III), a raw material (hereinafter, also referred to "Z raw material") comprising at least one element selected from the group consisting of W, La, Ce, Yb, and Y (hereinafter, also referred to as "component Z") may further be mixed. The Z raw material is not limited to the following as long as it is a substance containing a component Z, and examples thereof include: a compound containing a component Z; and a metal of the component Z, the metal being made soluble by an adequate reagent. Examples of the compound containing a component Z include, but are not limited to, ammonium salts, nitric acid salts, carboxylic acid salts, ammonium carboxylates, peroxocarboxylic acid salts, ammonium peroxocarboxylates, halogenated ammonium salts, halides, acetylacetonate, and alkoxides. Among these, water-soluble raw materials such as nitric acid salts and carboxylic acid salts are preferable.

In at least one of sub-step (I), sub-step (II), and sub-step (III), the raw material ratio is preferably regulated such that an oxide catalyst obtained through step (V), which will be described later, has a composition represented by the following formula (1). By using the oxide catalyst having a composition represented by the following formula (1), there is a tendency that the yield of an unsaturated nitrile is further improved.

$$Mo_1V_aNb_bSb_cT_dZ_eO_n \qquad (1)$$

wherein T represents at least one element selected from Ti, W, Mn, and Bi; Z represents at least one element selected from La, Ce, Yb, and Y; a, b, c, d, and e represent atomic ratios of respective elements when an atomic ratio of Mo is 1, and are in the range of 0.05≤a≤0.3, 0.01≤b≤0.15, 0.05≤c≤0.3, 0≤d≤0.1, and 0≤e≤0.1 respectively; and n represents a value satisfying a balance of atomic valences.

The composition of the oxide catalyst which is obtained after step (V) may be different from the composition of the oxide catalyst which is finally obtained. That is, the composition of a protrusion, which will be described later, of the oxide catalyst and the composition of the main body of the oxide catalyst are different because the composition of the oxide catalyst before step (VI) of removing this protrusion is changed after step (VI). In at least one of sub-step (I), sub-step (II), and sub-step (III), the composition ratio may be set in consideration of the change as well. The "protrusion" in the present specification refers to matter that has oozed out at and/or adhered to the surface of a calcined body obtained through main calcination, which will be described later, or matter that has protruded from and/or adhered to the surface of a calcined body.

Hereinafter, in the raw material preparation step, description will be made taking as an example a case where the aqueous mixed liquid (C) comprising a Mo raw material, a V raw material, an Sb raw material, a Nb raw material, and a Z raw material is prepared using water as a solvent and/or a dispersion medium. However, the raw material preparation step is not limited to this.

In a case where powdery silica is added, powdery silica is preferably added after hydrogen peroxide water and the Nb raw material liquid (B) are added to the aqueous mixed liquid (A). In addition, powdery silica can be added as it is, but is more preferably added as a liquid in which the powdery silica is dispersed in water, that is, as a powdery silica-containing suspension. The concentration of powdery silica in the powdery silica-containing suspension on this occasion is preferably 1.0% by mass or more and 30% by mass or less, and more preferably 3.0% by mass or more and 20% by mass or less. When the concentration of powdery silica is 1.0% by mass or more, there is a tendency that it can be thereby suppressed that the shape of the catalyst particle becomes distorted due to a low viscosity of the aqueous mixed liquid (C). In addition, there is a tendency that occurrence of a depression in the catalyst particle can also be suppressed. When the concentration of powdery silica is 30% by mass or less, there is a tendency that gelation of the aqueous mixed liquid (C) and clogging of the aqueous mixed liquid (C) in piping, the gelation and the clogging being attributable to a high viscosity of the aqueous mixed liquid (C), can be thereby suppressed, and there is a tendency that the dried powder can be thereby easily obtained. Further, there is a tendency that the performance of the oxide catalyst is further improved.

In the present embodiment, ammonia can be added to the aqueous mixed liquid (A), the Nb raw material liquid (B), or the aqueous mixed liquid (C). From the viewpoint of properly keeping the dissolution state of the metals in the aqueous mixed liquid (A), the viewpoint of properly keeping the degree of reduction of the metals, and other viewpoints, ammonia is more preferably added to the aqueous mixed liquid (C). The timing of addition to the aqueous mixed liquid can be appropriately adjusted.

As the amount of NH to be added, addition in an amount of 0.1 or more and 5 or less as the molar ratio of $NH_3/Nb$ is preferable. The molar ratio is more preferably 0.2 or more and 4.5 or less, and still more preferably 0.3 or more and 3 or less. By setting the molar ratio to 5 or less, the degree of reduction of metals can be properly kept, it can be prevented that the proper oxidation-reduction states of the metal components in the liquid cannot be maintained because $NH_3$ decomposes hydrogen peroxide in the aqueous mixed liquid, and it can be prevented that the shape of the catalyst particle becomes distorted because the viscosity of the aqueous mixed liquid increases to make it hard to feed the aqueous mixed liquid in the drying step.

The resultant aqueous mixed liquid (C) may be subjected to an aging treatment. Aging of the aqueous mixed liquid (C) refers to leaving the aqueous mixed liquid (C) to stand or stirring the aqueous mixed liquid (C) for a predetermined time. The aging time is preferably 5 minutes or more and 50 hours or less, and more preferably 5 minutes or more and 6 hours or less. When the aging time is in the range, there is a tendency that the aqueous mixed liquid (C) having a suitable oxidation-reduction state (potential) becomes easily formed, and the catalyst performance of a resultant composite oxide is further improved.

In a case where the oxide catalyst is industrially produced via drying with a spray-drier herein, the treatment speed of the spray drier usually controls the speed of production, and there is a tendency that it takes time for the spray-drying of all the aqueous mixed liquid (C) to be completed after part of the mixed liquid is spray-dried. During the spray-drying, aging of the aqueous mixed liquid which has not been subjected to the spray-drying treatment yet is continued. Accordingly, the aging time not only includes the aging time before drying in step (IV), which will be described later, but also includes the time from the start to the completion of drying.

In addition, the aging temperature is preferably 25° C. or more from the viewpoint of preventing condensation of the Mo component or precipitation of the metal oxide due to V and the other metal species or a plurality of metals. In addition, from the viewpoint of forming the aqueous mixed liquid (C) of a preferred embodiment while making the rate of precipitation of Nb due to hydrolysis of a complex containing Nb and hydrogen peroxide fall within a proper range, the aging temperature is preferably set to 75° C. or less, and more preferably 70° C. or less. By extending the aging time, raising the temperature of aging, or combining and performing these, the catalyst can be further reduced after calcination.

In addition, according to diligent studies conducted by the present inventors, it has been found that there is a tendency that the reduction rate of the catalyst after calcination and the oxidation-reduction potential of the aqueous mixed liquid (C) have a certain correlation. When the oxidation-reduction potential of the aqueous mixed liquid (C) becomes high, the catalyst after calcination leans toward an oxidation direction, and when the oxidation-reduction potential of the aqueous mixed liquid (C) becomes low, the catalyst after calcination leans toward a reduction direction. Therefore, the oxidation-reduction potential of the aqueous mixed liquid (C) is preferably less than 450 mV, more preferably 150 mV or more and less than 450 mV, still more preferably 170 mV or more and less than 445 mV, and further still more preferably 200 mV or more and 440 mV or less. The oxidation-reduction potential of the aqueous mixed liquid (C) can be measured by using, but not particularly limited to, a potentiometer sold on the market. Specifically, the oxidation-reduction potential is measured by the method described in Examples, which will be described later.

[Step (IV): Drying Step]

Step (IV) in the present embodiment is a step of drying the aqueous mixed liquid (C), thereby obtaining a dried powder. Drying can be performed by known methods and can also be conducted, for example, by spray-drying or evaporation to dryness. In a case where a fluidized bed reaction system is adopted in a gas-phase catalytic oxidation reaction or gas-phase catalytic ammoxidation reaction in which the oxide catalyst is used, a fine, spherical dried powder is preferably obtained in step (IV) from the viewpoint of making the fluidity in a reactor into a preferred state, or other viewpoints. From the viewpoint of obtaining a fine, spherical dried powder, spray-drying is preferably adopted. Nebulization in the spray-drying method may be any of a centrifugal system, a two-fluid nozzle system, and a high-pressure nozzle system. As a heat source for drying, air heated with steam, an electric heater, or the like can be used.

The spray velocity, the rate of feeding the aqueous mixed liquid (C), the number of rotations of an atomizer in the case of a centrifugal system, and the like are preferably adjusted such that the size of a resultant dried powder becomes suitable. The average particle diameter of the dried powder is preferably 35 μm or more and 75 μm or less, more preferably 40 μm or more and 70 μm or less, and still more preferably 45 μm or more and 65 μm or less. The average particle diameter does not change so much even after calcination. Examples of the method of adjusting the average particle diameter of the dried powder include a method of performing classification, which will be described in Examples.

[Step (V): Calcination Step]

Step (V) in the present embodiment is a step of calcining the dried powder under an inert gas atmosphere. As a calcination apparatus for calcining the dried powder, a rotary furnace (rotary kiln) for example can be used. The shape of a calcination vessel in which the dried powder is calcined is not particularly limited, but the calcination vessel is preferably pipe-shaped (calcination pipe) from the viewpoint of enabling continuous calcination, and more preferably cylindrically shaped. As a heating system, an external heating type is preferable from the viewpoint of easiness of adjusting the calcination temperature in such a way as to make a temperature-raising pattern preferable, and an electric furnace can be suitably used as an external heat source. The size, the material, and the like of the calcination pipe can be appropriately selected according to the calcination conditions and the quantity of production.

In step (V), the calcination is preferably performed by being divided into two stages. When the first calcination is referred to as pre-stage calcination, and the latter calcination is referred to as main calcination, it is preferable that the pre-stage calcination be performed in a temperature range of 250° C. or more and 400° C. or less, and the main calcination be performed in a temperature range of 450° C. or more and 700° C. or less. The pre-stage calcination and the main calcination may be performed continuously, or the main calcination may be performed afresh after the pre-stage calcination is once completed. Alternatively, each of the pre-stage calcination and the main calcination may be divided into several stages.

With respect to the calcination atmosphere, the calcination is preferably performed while an inert gas, such as nitrogen, which does not substantially contain oxygen is circulated from the viewpoint of adjusting the oxidation-reduction state into a preferred one. In a case where the calcination is performed batch-wise, the feed rate of the inert gas is preferably 50 NL/hr. or more, more preferably 50 NL/hr. or more and 5000 NL/hr. or less, and still more preferably 50 NL/hr. or more and 3000 NL/hr. or less per kg of the dried powder from the viewpoint of adjusting the oxidation-reduction state into a preferred one. The "NL" herein means volume of a gas measured at the normal temperature and pressure conditions, namely at 0° C. and 1 atm.

The reduction rate of a calcined body (pre-stage calcined body) after the pre-stage calcination is preferably 7.0% or more and 15% or less, more preferably 8.0% or more and 12% or less, and still more preferably 9.0% or more and 12% or less. When the reduction rate is in this range, there is a tendency that the activity of the oxide catalyst is thereby further improved, and the catalyst production efficiency is thereby further improved. Examples of a method of controlling the reduction rate in a desired range include, but are not limited to, a method of adjusting the pre-stage calcination temperature, a method of adjusting the amount of an inert gas which is circulated during calcination, a method of adding an oxidative component during the calcination or before the calcination, and a method of adding a reductive component during the calcination or before the calcination. In addition, these may be combined.

[Step (VI): Removal Step]

In step (VI) optionally performed in the present embodiment, a protrusion existing at the surface of a particle of the oxide catalyst is removed. Most of the protrusions are protruded crystals of an oxide or other impurities. Particularly in the case of a calcined body containing a plurality of metals, an oxide having a composition which is different from that of the crystal which forms most part of the calcined body may be formed in some cases in a form such that the oxide has oozed out of the main body part of the calcined body. There is a tendency that such a protrusion becomes a factor of lowering the fluidity. Therefore, by removing the protrusion from the surface of the oxide catalyst, there is a tendency that the performance of the oxide catalyst gets higher. In a case where the removal of the protrusion is performed in a gram scale, the apparatus described below can be used. That is, a perpendicular tube provided with a holed board having at least one hole at the bottom portion thereof and having a paper filter installed at the upper portion can be used. By loading the calcined body into this perpendicular tube and circulating air from below, air flows from each hole to facilitate contact among calcined bodies, and the removal of the protrusion is performed.

[Oxide Catalyst]

The oxide catalyst according to the present embodiment is obtained by the above-described method for producing an oxide catalyst. The resultant oxide catalyst preferably has a composition represented by the following formula (1).

$$MoV_aNb_bSb_cT_dZ_eO_n \quad (1)$$

wherein T represents at least one element selected from Ti, W, Mn, and Bi; Z represents at least one element selected from La, Ce, Yb, and Y; a, b, c, d, and e represent atomic ratios of respective elements when an atomic ratio of Mo is 1, and are in the range of $0.05 \leq a \leq 0.3$, $0.01 \leq b \leq 0.15$, $0.05 \leq c \leq 0.3$, $0 \leq d \leq 0.1$, and $0 \leq e \leq 0.1$ respectively; and n represents a value satisfying a balance of atomic valences.

The composition of the oxide catalyst can be measured with fluorescent X-ray analysis (trade name "RIX1000" manufactured by Rigaku Corporation, Cr tube, tube voltage of 50 kV, tube current of 50 mA).

The oxide catalyst preferably comprises 30% by mass or more and 70% by mass or less of a carrier based on the total amount (100% by mass) of the oxide catalyst. To obtain the oxide catalyst that is in such a range, the oxide catalyst preferably comprises 30% by mass or more and 70% by mass or less of silica, such as silica sol and powdery silica, in terms of $SiO_2$, and the oxide catalyst may more preferably use 40% by mass or more and 60% by mass or less of silica and may still more preferably use 45% by mass or more and 55% by mass or less of silica. When the oxide catalyst comprises 30% by mass or more of the carrier, there is a tendency that the strength of the oxide catalyst is thereby further improved, and when the oxide catalyst comprises 70% by mass or less of the carrier, there is a tendency that the oxide catalyst thereby has a higher activity.

The content of the carrier in the oxide catalyst can be determined, for example, by measurement with fluorescent X-ray analysis (trade name "RIX1000" manufactured by Rigaku Corporation, Cr tube, tube voltage of 50 kV, tube current of 50 mA).

[Method for Producing Unsaturated Acid or Unsaturated Nitrile]

The method for producing an unsaturated acid or an unsaturated nitrile according to the present embodiment comprises: a step of obtaining an oxide catalyst by the method for producing an oxide catalyst according to the present embodiment; and a production step of producing an unsaturated acid or an unsaturated nitrile corresponding to propane or isobutane through a gas-phase catalytic oxidation reaction or gas-phase catalytic ammoxidation reaction of propane or isobutane in the presence of the produced oxide catalyst. In addition, the production step is preferably a step of producing an unsaturated nitrile through a gas-phase catalytic ammoxidation reaction of propane or isobutane. Hereinafter, a method for producing acrylonitrile as the unsaturated nitrile using the oxide catalyst according to the present embodiment filled in a reactor will be described.

<Gas-Phase Catalytic Oxidation Reaction and Gas-Phase Catalytic Ammoxidation Reaction>

Propane or isobutane, and oxygen are used for a gas-phase catalytic oxidation reaction, and propane or isobutane; ammonia; and oxygen are used for a gas-phase catalytic ammoxidation reaction. Among them, propane and ammonia do not necessarily have to be of high purity, and may be industrial-grade gasses such as propane containing 3% by volume of an impurity such as ethane, ethylene, n-butane, or isobutane; and ammonia containing 3% by volume of an impurity such as water. Examples of oxygen include, but are not limited to: air, oxygen-enriched air, and pure oxygen; and gases obtained by diluting these with an inert gas such as helium, argon, carbon dioxide, or nitrogen, or water vapor. Among these, in the case of use in an industrial scale, air is preferable because of simplicity.

The reaction conditions in the gas-phase catalytic oxidation reaction are not particularly limited, and examples thereof include the following conditions. The molar ratio of oxygen to be supplied for the reaction to propane or isobutane, (oxygen/(propane and isobutane)), is preferably 0.1 or more and 6.0 or less, and more preferably 0.5 or more and 4.0 or less. The reaction temperature is preferably 300° C. or more and 500° C. or less, and more preferably 350° C. or more and 500° C. or less. The reaction pressure is preferably $5.0 \times 10^4$ Pa or more and $5.0 \times 10^5$ Pa or less, and more preferably $1.0 \times 10^5$ Pa or more and $3.0 \times 10^5$ Pa or less. The contact time is preferably 0.1 sec·g/cm$^3$ or more and 10 sec·g/cm$^3$ or less, and more preferably 0.5 sec·g/cm$^3$ or more and 5.0 sec·g/cm$^3$ or less. By setting the reaction conditions to the ranges, there is a tendency that production of a by-product is further suppressed, and the yield of an unsaturated nitrile can be further improved.

In the present embodiment, the contact time is defined by the following expression.

Contact time (sec·g/cm$^3$)=($W/F$)×273/(273+$T$)

W, F, and T herein are defined as follows.
W=amount (g) of catalyst filled
F=flow rate (Ncm$^3$/sec) of raw material mixed gas at the normal state (0° C., $1.013 \times 10^5$ Pa)
T=reaction temperature (° C.)

The conversion rate of alkane such as propane or isobutane, and the unsaturated acid or unsaturated nitrile yield follow the following definition.

Conversion rate (%) of alkane=(number of moles of alkane reacted)/(number of moles of alkane supplied)×100

Unsaturated acid or unsaturated nitrile yield (%)= (number of moles of unsaturated acid or unsaturated nitrile produced)/(number of moles of alkane supplied)×100

The reaction conditions in the gas-phase catalytic ammoxidation reaction are not particularly limited, and examples thereof include the following conditions. The molar ratio of oxygen to be supplied for the reaction to propane or isobutane, (oxygen/(propane and isobutane)), is preferably 0.1 or more and 6.0 or less, and more preferably 0.5 or more and 4.0 or less. The molar ratio of ammonia to be supplied for the reaction to propane or isobutane, (ammonia/(propane and isobutane)), is preferably 0.3 or more and 1.5 or less, and more preferably 0.7 or more and 1.2 or less. The reaction temperature is preferably 320° C. or more and 500° C. or less, and more preferably 370° C. or more and 460° C. or less. The reaction pressure is preferably $5.0 \times 10^4$ Pa or more and $5.0 \times 10^5$ Pa or less, and more preferably $1.0 \times 10^5$ Pa or more and $3.0 \times 10^5$ Pa or less. The contact time is preferably 0.1 sec·g/cm$^3$ or more and 10 sec·g/cm$^3$ or less, and more preferably 0.5 sec·g/cm$^3$ or more and 5.0 sec·g/cm$^3$ or less. By setting the reaction conditions to the ranges, there is a tendency that production of a by-product is further suppressed, and the yield of an unsaturated nitrile can be further improved.

As a reaction system in the gas-phase catalytic oxidation reaction and the gas-phase catalytic ammoxidation reaction, known systems such as a fixed bed, a fluidized bed, and a moving bed can be adopted. Among these, a fluidized bed reactor in which the heat of reaction is easily removed is preferable. In addition, the gas-phase catalytic ammoxidation reaction may be a single current type or a recycling type. In the case of the recycling system, the method of separating and collecting an unreacted alkane is not particularly limited, and a method using a pressure swing adsorption unit (PSA) or the like, a method of performing separation with a membrane, a method of performing adsorption to a solvent, and the like can be adopted. In the method of performing separation with a membrane, any of organic membranes and inorganic membranes may be used, and separation with a zeolite membrane to which silver or phosphorus is adsorbed may be used. In the case of the method of performing adsorption to a solvent, a stripping operation can be performed with stream after performing adsorption to a water-insoluble, nonpolar, organic solvent.

EXAMPLES

Hereinafter, the present embodiment will be described in further detail giving specific Examples and Comparative Examples, but the present embodiment is not limited by the following Examples and Comparative Examples within a range not exceeding the scope thereof. Various physical properties and evaluations in the Examples and the Comparative Examples, which will be described later, were measured according to the following methods.

(Preparation Example) Niobium Raw Material Liquid

A niobium raw material liquid was prepared according to the following method. Into 10 kg of water, 1.420 kg of niobic acid containing 79.8% by mass of Nb$_2$O$_5$ and 5.134 kg of oxalic acid dihydrate (H$_2$C$_2$O$_4$·2H$_2$O) were mixed. The molar ratio of oxalic acid/niobium added was 4.8, and the concentration of niobium added was 0.52 mol/kg. This liquid was heated and stirred at 95° C. for 2 hours to thereby obtain a mixed liquid containing niobium dissolved therein. This mixed liquid was left to stand and cooled with ice, and thereafter a solid was separated by suction filtration to obtain a uniform niobium raw material liquid. The molar ratio of oxalic acid/niobium in this niobium raw material liquid was found to be 2.340 by the analysis described below. The resultant niobium raw material liquid was used as a niobium raw material liquid (B$_1$) in producing oxide catalysts of Examples 1 to 9 and Comparative Examples 1 to 7 below.

(Physical Property 1) Concentration of Niobium and Concentration of Oxalic Acid

Into a melting pot, 10 g of the niobium raw material liquid (B$_1$) obtained above was precisely weighed, and was dried at 95° C. overnight, and thereafter a heat treatment was performed at 600° C. for 1 hour to obtain 0.8125 g of Nb$_2$O$_5$. From this result, the concentration of niobium was found to be 0.611 mol (Nb)/kg (niobium raw material liquid (B$_1$)). In addition, 3 g of this niobium raw material liquid (B$_1$) was precisely weighed into a 300-mL glass beaker, 200 mL of approximately 80° C. hot water was added thereto, and subsequently 10 mL of 1:1 sulfuric acid was added thereto. A resultant mixed liquid was titrated under stirring using 1/4 N KMnO$_4$ while keeping the liquid temperature at 70° C. on a hot stirrer. A point where a slight, pale pink color by KMnO$_4$ continued for approximately 30 seconds or more was determined to be an end point. The concentration of oxalic acid was determined from the titer by calculation according to the following formula and was found to be 1.430 mol (oxalic acid)/kg (niobium raw material liquid (B$_1$)).

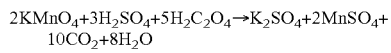

$$2KMnO_4 + 3H_2SO_4 + 5H_2C_2O_4 \rightarrow K_2SO_4 + 2MnSO_4 + 10CO_2 + 8H_2O$$

(Physical Property 2) Oxidation-Reduction Potential of Aqueous Mixed Liquids (A$_1$') and (C$_1$)

The oxidation-reduction potential of the aqueous mixed liquids (A$_1$') and (C$_1$) was measured using a potentiometer sold on the market (manufactured by DKK-TOA CORPORATION).

(Physical Property 3) Composition of Oxide Catalysts

The composition of the oxide catalysts was measured with fluorescent X-ray analysis (trade name "RIX1000" manufactured by Rigaku Corporation, Cr tube, tube voltage of 50 kV, tube current of 50 mA).

(Physical Property 4) Amount of Carrier

The amount of a carrier is defined as the amount of the carrier (% by mass) based on the total amount (100% by mass) of the oxide catalyst obtained in each of the Examples and the Comparative Examples, which will be described later, and the resultant oxide catalyst was subjected to measurement by fluorescent X-ray analysis (trade name "RIX1000" manufactured by Rigaku Corporation, Cr tube, tube voltage of 50 kV, tube current of 50 mA) to determine the amount of the carrier.

(Evaluation) Yield of Acrylonitrile (Unsaturated Nitrile)

In the Examples and the Comparative Examples, the yield of acrylonitrile was determined as follows. A gas of acrylonitrile the concentration of which was already known was analyzed by gas chromatography (GC: product name "GC2014" manufactured by SHIMADZU CORPORATION) to get a calibration curve in advance, and thereafter a gas produced through the ammoxidation reaction was quantitatively injected into the GC to measure the number of moles of acrylonitrile produced. The yield of acrylonitrile was determined from the measured number of moles of acrylonitrile according to the following expression.

Yield (%) of acrylonitrile=(number of moles of acrylonitrile produced)/(number of moles of propane supplied)×100

(Example 1)
(Preparation Step) Aqueous Mixed Liquid (A$_1$)

To 1721 g of water, 492.7 g of ammonium heptamolybdate [(NH$_4$)$_6$Mo$_7$O$_{24}$.4H$_2$O], 63.2 g of ammonium metavanadate [NH$_4$VO$_3$], 95.1 g of diantimony trioxide [Sb$_2$O$_3$], and 9.8 g of cerium nitrate [Ce(NO$_3$)$_3$.6H$_2$O] were added and heated at 95° C. for 2 hours while being stirred to prepare an aqueous mixed liquid (A$_1$).

(Mixing Step) Aqueous Mixed Liquid (C$_1$)

The resultant aqueous mixed liquid (A$_1$) was cooled to 70° C., thereafter 871.0 g of silica sol containing 34.1% by mass of SiO$_2$ was added to the aqueous mixed liquid (A$_1$), and further, 131.6 g of hydrogen peroxide water containing 30% by mass of H$_2$O$_2$ was added thereto at the point in time when the liquid temperature reached 55° C. to obtain an aqueous mixed liquid (A$_1$'). The oxidation-reduction potential of this aqueous mixed liquid (A$_1$') was measured. Immediately after that, the niobium raw material liquid (B$_1$), 38.4 g of ammonium metatungstate aqueous solution (purity of 50%), and a dispersion liquid obtained by dispersing 297.0 g of powdery silica in 2673.0 g of water were added in sequence to the aqueous mixed liquid (A$_1$'), thereafter 37.0 g of 25% ammonia water was added, and a resultant mixture was subjected to aging by stirring at 65° C. for 2.5 hours to obtain an aqueous mixed liquid (C$_1$) in the form of a slurry. The oxidation-reduction potential of this aqueous mixed liquid (C$_1$) was measured.

(Drying Step) Dried Powder (D$_1$)

The resultant aqueous mixed liquid (C$_1$) was supplied to a centrifugal spray drier (the heat source for drying is air, and the same heat source for drying was used in the following centrifugal spray driers) to be dried to obtain a fine, spherical dried powder (D$_1$). The temperature at the inlet of the drier was 210° C., and the temperature at the outlet was 120° C.

The resultant dried powder (D$_1$) was classified using a sieve having an opening of 25 μm to obtain a dried powder (E$_1$) being a classified product. The resultant dried powder (E$_1$) had a percentage content of particles of 25 μm or less of 0.2% by mass and an average primary particle diameter of 54 μm. The percentage content of particles and the average particle diameter were measured with "LS230," trade name, manufactured by Beckman Coulter, Inc. (the following percentage contents of particles and average particle diameters were measured in the same manner).

(Calcination Step) Oxide Catalyst (F$_1$)

The resultant dried powder (E$_1$) was supplied to a continuous SUS cylindrical calcination pipe having a diameter (inner diameter; the following diameters were the same) of 3 inches and a length of 89 cm at a feed rate of 80 g/hr in a rotary furnace. Into the calcination pipe, a nitrogen gas of 1.5 NL/min was allowed to flow in each of the direction opposite to the direction of feeding the dried powder (namely countercurrent; the same applies to the following directions opposite) and the same direction as the direction of feeding the dried powder (namely, parallel current; the same applies to the following same directions) to make the total flow rate 3.0 NL/min. The pre-stage calcination was performed by setting the temperature of the furnace such that the temperature can be raised to 360° C. being the highest calcination temperature in 4 hours while the calcination pipe was rotated at a rate of 4 rotations/min, and the temperature can be held at 360° C. for 1 hour. A small amount of the pre-stage calcined body collected at the outlet of the calcination pipe was sampled and heated to 400° C. under a nitrogen atmosphere, and thereafter the reduction rate was measured and found to be 10.1%. The collected pre-stage calcined body was supplied to a continuous SUS calcination pipe having a diameter of 3 inches and a length of 89 cm at a feed rate of 60 g/hr in a rotary furnace. Into the calcination pipe, a nitrogen gas of 1.1 NL/min was allowed to flow in each of the direction opposite to the direction of feeding the dried powder and the same direction as the direction of feeding the dried powder to make the total flow rate 2.2 NL/min. The main calcination was performed by setting the temperature of the furnace such that the temperature can be raised to 680° C. in 2 hours, held at 680° C. for 2 hours, and thereafter lowered to 600° C. in 8 hours, and thus an oxide catalyst (F$_1$) was obtained.

(Removal Step)

Into a perpendicular tube (inner diameter of 41.6 mm, length of 70 cm), which is provided with a holed disk at the bottom portion thereof, the holed disk including 3 holes having a diameter of 1/64 inches, and which has a paper filter installed at the upper portion thereof, 50 g of the oxide catalyst ($F_1$) was loaded. Subsequently, air was circulated upward from below via each hole of the perpendicular tube at room temperature to facilitate contact among calcined bodies. The length of the air current on that occasion in the flowing direction of the air current was 56 mm, and the average linear velocity of the air current was 332 m/s. A protrusion did not exist in the oxide catalyst ($F_1$) obtained after 24 hours. The composition on that occasion was $Mo_1V_{0.195}Nb_{0.110}Sb_{0.234}W_{0.04}Ce_{0.008}O_n$, and the amount of the carrier was 50.8%.

(Production Step) Ammoxidation Reaction of Propane

Propane was subjected to a gas-phase catalytic ammoxidation reaction according to the following method using the oxide catalyst ($F_1$) obtained above. In a Vycor glass fluidized bed type reaction pipe having an inner diameter of 25 mm, 38 g of the oxide catalyst was filled, and a mixed gas having a molar ratio of propane:ammonia:oxygen:helium=1:1:2.9:18 was supplied at a contact time of 3.0 (sec·g/cm$^3$), reaction temperature of 445° C., and a reaction pressure of 40 kPa.

The potential at the time when loading the niobium raw material liquid ($B_1$) was started, and the reaction yield of acrylonitrile (AN) obtained when the reaction was performed for consecutive 10 days with respect to this catalyst ($F_1$) are shown in Table 1.

(Example 2)

An oxide catalyst was produced in the same manner as in Example 1 except that stirring was performed at 55° C. for 4 minutes after loading hydrogen peroxide water in Example 1, and thereafter the niobium raw material liquid ($B_1$) was added. The potential at the time when loading the niobium raw material liquid ($B_1$) was started and the reaction yield of acrylonitrile (AN) obtained when the ammoxidation reaction of propane was performed in the same manner as in Example 1 with respect to this oxide catalyst are shown in Table 1.

(Example 3)

An oxide catalyst was produced in the same manner as in Example 1 except that the amount of hydrogen peroxide water loaded in Example 1 was changed to 51.7 g. The potential at the time when loading the niobium raw material liquid ($B_1$) was started and the reaction yield of acrylonitrile (AN) obtained when the ammoxidation reaction of propane was performed in the same manner as in Example 1 with respect to this oxide catalyst are shown in Table 1.

(Example 4)

An oxide catalyst was produced in the same manner as in Example 1 except that the amount of hydrogen peroxide water loaded in Example 1 was changed to 73.8 g. The potential at the time when loading the niobium raw material liquid ($B_1$) was started and the reaction yield of acrylonitrile (AN) obtained when the ammoxidation reaction of propane was performed in the same manner as in Example 1 with respect to this oxide catalyst are shown in Table 1.

(Example 5)

An oxide catalyst was produced in the same manner as in Example 1 except that the amount of hydrogen peroxide water loaded in Example 1 was changed to 221.5 g. The potential at the time when loading the niobium raw material liquid ($B_1$) was started and the reaction yield of acrylonitrile (AN) obtained when the ammoxidation reaction of propane was performed in the same manner as in Example 1 with respect to this oxide catalyst are shown in Table 1.

(Example 6)

An oxide catalyst was produced in the same manner as in Example 2 except that the aging by stirring in Example 2 was performed at 60° C. for 2 hours. The potential at the time when loading the niobium raw material liquid ($B_1$) was started and the reaction yield of acrylonitrile (AN) obtained when the ammoxidation reaction of propane was performed in the same manner as in Example 1 with respect to this oxide catalyst are shown in Table 1.

(Example 7)

An oxide catalyst was produced in the same manner as in Example 1 except that the amount of hydrogen peroxide water loaded in Example 1 was changed to (109.7) g. The potential at the time when loading the niobium raw material liquid ($B_1$) was started and the reaction yield of acrylonitrile (AN) obtained when the ammoxidation reaction of propane was performed in the same manner as in Example 1 with respect to this oxide catalyst are shown in Table 1.

(Example 8)

An oxide catalyst was produced in the same manner as in Example 1 except that stirring was performed at 55° C. for 1 minute after loading hydrogen peroxide water in Example 1, and thereafter the niobium raw material liquid ($B_1$) was added. The potential at the time when loading the niobium raw material liquid ($B_1$) was started and the reaction yield of acrylonitrile (AN) obtained when the ammoxidation reaction of propane was performed in the same manner as in Example 1 with respect to this oxide catalyst are shown in Table 1.

(Example 9)

An oxide catalyst was produced in the same manner as in Example 1 except that stirring was performed at 55° C. for 2 minutes after loading hydrogen peroxide water in Example 1, and thereafter the niobium raw material liquid ($B_1$) was added. The potential at the time when loading the niobium raw material liquid ($B_1$) was started and the reaction yield of acrylonitrile (AN) obtained when the ammoxidation reaction of propane was performed in the same manner as in Example 1 with respect to this oxide catalyst are shown in Table 1.

(Comparative Example 1)

An oxide catalyst was produced in the same manner as in Example 1 except that stirring was performed at 55° C. for 30 minutes after loading hydrogen peroxide water in Example 1, and thereafter the niobium raw material liquid ($B_1$) was loaded. The potential at the time when loading the niobium raw material liquid ($B_1$) was started and the reaction yield of acrylonitrile (AN) obtained when the ammoxidation reaction of propane was performed in the same manner as in Example 1 with respect to this oxide catalyst are shown in Table 1.

(Comparative Example 2)

An oxide catalyst was produced in the same manner as in Example 1 except that hydrogen peroxide water was not loaded in Example 1, and at the potential described in Table 1, the niobium raw material liquid ($B_1$) was added before loading silica sol. The potential at the time when loading the niobium raw material liquid ($B_1$) was started and the reaction yield of acrylonitrile (AN) obtained when the ammoxidation reaction of propane was performed in the same manner as in Example 1 with respect to this oxide catalyst are shown in Table 1.

(Comparative Example 3)

An oxide catalyst was produced in the same manner as in Example 1 except that stirring was performed at 55° C. for 30 minutes after loading hydrogen peroxide water in Example 1, the niobium raw material liquid ($B_1$) was thereafter loaded, and the aging by stirring was performed at 65° C. for 8 hours. The potential at the time when loading the niobium raw material liquid ($B_1$) was started and the reaction yield of acrylonitrile (AN) obtained when the ammoxidation reaction of propane was performed in the same manner as in Example 1 with respect to this oxide catalyst are shown in Table 1.

(Comparative Example 4)

An oxide catalyst was produced in the same manner as in Example 1 except that hydrogen peroxide water was not loaded in Example 1, and at the potential described in Table 1, the niobium raw material ($B_1$) was added before loading silica sol to perform the aging by stirring at 60° C. for 1.5 hours. The potential at the time when loading the niobium raw material liquid ($B_1$) was started and the reaction yield of acrylonitrile (AN) obtained when the ammoxidation reaction of propane was performed in the same manner as in Example 1 with respect to this oxide catalyst are shown in Table 1.

(Comparative Example 5)

An oxide catalyst was produced in the same manner as in Example 1 except that the amount of hydrogen peroxide water loaded in Example 1 was changed to (109.7) g, stirring was performed at 55° C. for 30 minutes after loading hydrogen peroxide water, and thereafter the niobium raw material liquid ($B_1$) was added. The potential at the time when loading the niobium raw material liquid ($B_1$) was started and the reaction yield of acrylonitrile (AN) obtained when the ammoxidation reaction of propane was performed in the same manner as in Example 1 with respect to this oxide catalyst are shown in Table 1.

(Comparative Example 6)

An oxide catalyst was produced in the same manner as in Example 1 except that stirring was performed at 55° C. for 5 minutes after loading hydrogen peroxide water in Example 1, and thereafter the niobium raw material liquid ($B_1$) was added. The potential at the time when loading the niobium raw material liquid ($B_1$) was started and the reaction yield of acrylonitrile (AN) obtained when the ammoxidation reaction of propane was performed in the same manner as in Example 1 with respect to this oxide catalyst are shown in Table 1.

(Comparative Example 7)

An oxide catalyst was produced in the same manner as in Example 1 except that stirring was performed at 55° C. for 10 minutes after loading hydrogen peroxide water in Example 1, and thereafter the niobium raw material liquid ($B_1$) was added. The potential at the time when loading the niobium raw material liquid ($B_1$) was started and the reaction yield of acrylonitrile (AN) obtained when the ammoxidation reaction of propane was performed in the same manner as in Example 1 with respect to this oxide catalyst are shown in Table 1.

TABLE 1

| | Potential, mV, of (A') before start of loading (B) | Amount of hydrogen peroxide $H_2O_2$/Sb | Time, min, elapsed from loading hydrogen peroxide to loading (B) | Potential, mV, of (C) immediately before spray-drying | AN yield % |
|---|---|---|---|---|---|
| Example 1 | 260 | 1.8 | 0 | 435 | 55.8 |
| Example 2 | 330 | 1.8 | 4 | 445 | 55.4 |
| Example 3 | 165 | 0.7 | 0 | 380 | 55 |
| Example 4 | 200 | 1 | 0 | 400 | 55.2 |
| Example 5 | 340 | 3 | 0 | 448 | 55.1 |
| Example 6 | 330 | 1.8 | 4 | 460 | 54.7 |
| Comparative Example 1 | 360 | 1.8 | 30 | 480 | 53.8 |
| Comparative Example 2 | 120 | 0 | 0 | 300 | 53.6 |
| Comparative Example 3 | 360 | 1.8 | 30 | 445 | 54.2 |
| Comparative Example 4 | 120 | 0 | 0 | 320 | 53.9 |
| Comparative Example 5 | 360 | 1.5 | 30 | 480 | 53.7 |
| Example 7 | 245 | 1.5 | 0 | 420 | 55.4 |
| Example 8 | 280 | 1.8 | 1 | 438 | 55.7 |
| Example 9 | 305 | 1.8 | 2 | 440 | 55.6 |
| Comparative Example 6 | 350 | 1.8 | 5 | 450 | 54.5 |
| Comparative Example 7 | 360 | 1.8 | 10 | 460 | 54.0 |

The invention claimed is:

1. A method for producing an oxide catalyst comprising Mo, V, Sb, and Nb, the method comprising:

a material preparation step comprising a sub-step (I) of preparing an aqueous mixed liquid (A) comprising Mo, V, and Sb, a sub-step (II) of adding hydrogen peroxide to the aqueous mixed liquid (A), thereby facilitating oxidation of the aqueous mixed liquid (A) and obtaining an aqueous mixed liquid (A'), and a sub-step (III) of mixing the aqueous mixed liquid (A') and a Nb material liquid (B), thereby obtaining an aqueous mixed liquid (C);

a drying step of drying the aqueous mixed liquid (C), thereby obtaining a dried powder; and a calcination step of calcining the dried powder under an inert gas atmosphere, wherein a time elapsed from addition of the hydrogen peroxide to the aqueous mixed liquid (A) to mixing the Nb material liquid (B) therewith is less than 5 minutes and the aqueous mixed liquid (A') before being subjected to the sub-step (III) has an oxidation-reduction potential of 150 to 350 mV.

2. The method for producing the oxide catalyst according to claim 1, wherein in the drying step, the aqueous mixed liquid (C) has an oxidation-reduction potential of less than 450 mV.

3. The method for producing the oxide catalyst according to claim 1, wherein the oxide catalyst is represented by the following formula (1):

$$Mo_1V_aNb_bSb_cT_dZ_eO_n \qquad (1)$$

wherein T represents at least one element selected from Ti, W, Mn, and Bi; Z represents at least one element selected from La, Ce, Yb, and Y; a, b, c, d, and e represent atomic ratios of respective elements when an atomic ratio of Mo is 1, and are in a range of $0.05 \leq a \leq 0.3$, $0.01 \leq b \leq 0.15$, $0.05 \leq c \leq 0.3$, $0 \leq d \leq 0.1$, and $0 \leq e \leq 0.1$ respectively; and n represents a value satisfying a balance of atomic valences.

4. The method for producing the oxide catalyst according to claim 1, wherein in the material preparation step, a carrier material is added to regulate a content of a carrier to be 30% by mass or more and 70% by mass or less based on a total amount of the oxide catalyst.

5. A method for producing an unsaturated acid or an unsaturated nitrile, the method comprising:
a step of obtaining the oxide catalyst by the method for producing the oxide catalyst according to claim 1; and
a production step wherein a gas-phase catalytic oxidation reaction or a gas-phase catalytic ammoxidation reaction of propane or isobutane are performed in a presence of the produced oxide catalyst to thereby produce the unsaturated acid or the unsaturated nitrile corresponding thereto.

* * * * *